United States Patent [19]
Wold

[11] Patent Number: 6,094,597
[45] Date of Patent: Jul. 25, 2000

[54] IMPLANTABLE MEDICAL DEVICE INCORPORATING DISTRIBUTED CORE, STEP-UP TRANSFORMER

[75] Inventor: Warren W. Wold, Edina, Minn.

[73] Assignee: Medtronic, Inc., Minneapolis, Minn.

[21] Appl. No.: 09/245,947

[22] Filed: Feb. 5, 1999

[51] Int. Cl.[7] ........................................... A61N 1/36
[52] U.S. Cl. ............................................... 607/5
[58] Field of Search ................................... 607/4, 5, 9

[56] References Cited

U.S. PATENT DOCUMENTS

| | | |
|---|---|---|
| 4,254,775 | 3/1981 | Langer . |
| 4,693,253 | 9/1987 | Adams . |
| 4,830,006 | 5/1989 | Haluska et al. . |
| 4,932,407 | 6/1990 | Williams . |
| 4,971,058 | 11/1990 | Pless et al. . |
| 5,265,588 | 11/1993 | Nelson et al. . |
| 5,312,441 | 5/1994 | Mader et al. . |
| 5,312,442 | 5/1994 | O'Phelan . |
| 5,370,663 | 12/1994 | Lin . |
| 5,370,669 | 12/1994 | Daglow et al. . |
| 5,405,363 | 4/1995 | Kroll et al. . |
| 5,527,346 | 6/1996 | Kroll . |
| 5,749,911 | 5/1998 | Westlund . |
| 5,827,326 | 10/1998 | Kroll . |

*Primary Examiner*—Scott M. Getzow
*Attorney, Agent, or Firm*—Reed A. Duthler; Harold R. Patton

[57] ABSTRACT

An implantable medical device (IMD) includes a distributed core, step-up transformer that is arranged within a hermetically sealed housing in space that would otherwise not be occupied and in a way that minimizes the size and weight of the IMD. The IMD preferably comprises an implantable cardioverter-defibrillator (ICD) of the type having a battery power source, a capacitor bank for storing a charge from the battery, and electronic circuitry coupled to the battery power supply and the capacitor bank for charging the capacitor bank through a step-up transformer and for discharging the capacitor bank into or around a patient's heart. The step up transformer comprises a plurality of distributed core step-up transformer modules which are miniaturized sufficiently to fit within small spaces of the housing cavity. The plurality of distributed core, step-up transformer modules are amenable to being arranged to fit into spaces within the cavity of the IMD housing that are not otherwise occupied. The space otherwise occupied by the bulky, prior art step-up transformer can than be occupied by other components or can result in making the housing itself smaller and possibly thinner in profile than it would otherwise be.

30 Claims, 5 Drawing Sheets

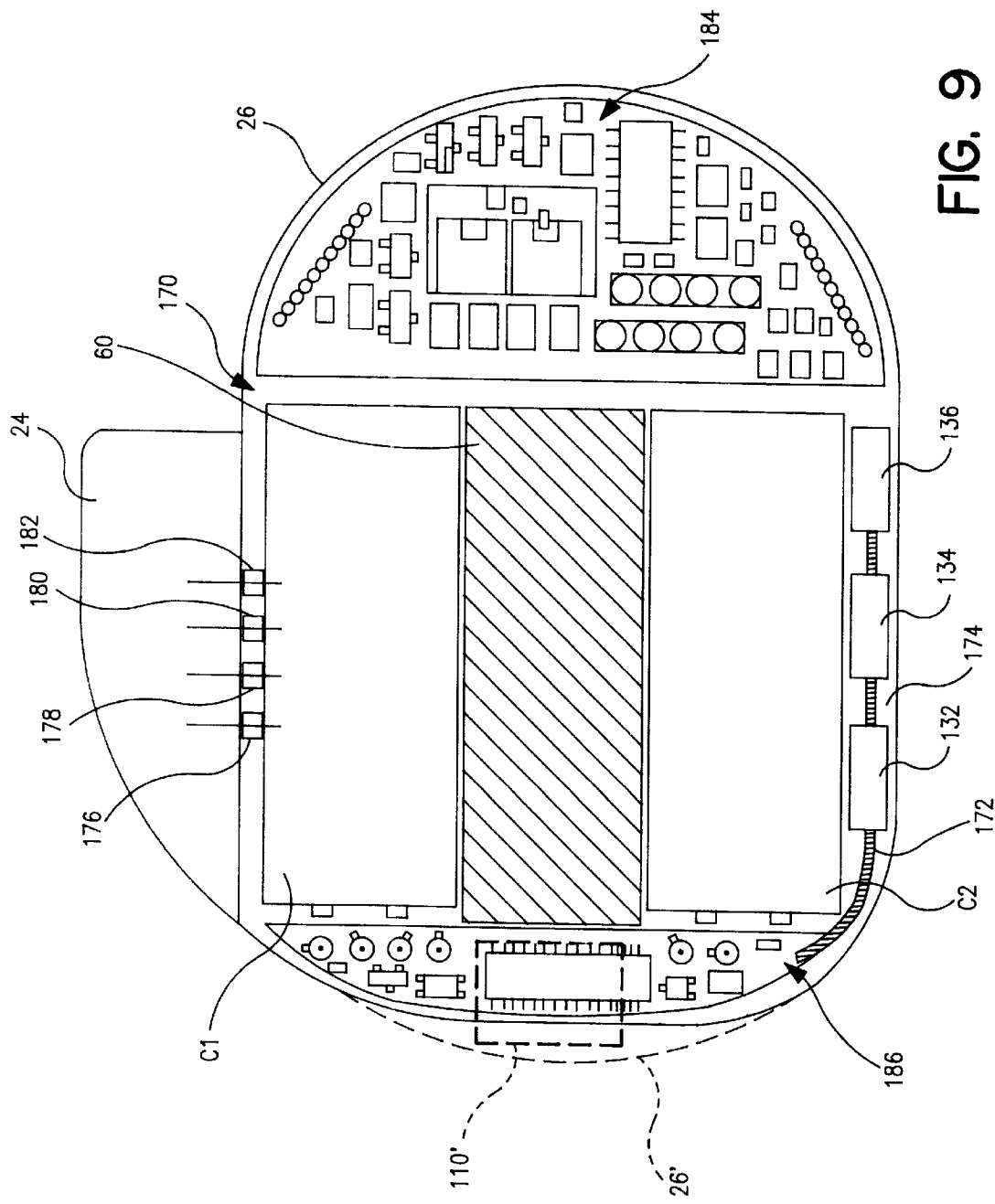

IMPLANTABLE MEDICAL DEVICE INCORPORATING DISTRIBUTED CORE, STEP-UP TRANSFORMER

FIELD OF THE INVENTION

This invention relates generally to implantable body tissue stimulating apparatus, and more particularly to an improved power converter transformer used in an implantable cardioverter/defibrillator (ICD) charging circuit for charging output capacitors thereof that is distributed, miniaturized and configured to occupy small spaces within the ICD housing to futher effect the miniaturization thereof.

BACKGROUND OF THE INVENTION

A wide variety of implantable medical devices (IMDs) that employ electronic circuitry for providing electrical stimulation of body tissue and/or monitoring a physiologic condition are known in the art. A number of IMDs of various types are known in the art for delivering electrical stimulating pulses to selected body tissue and typically comprise an implantable pulse generator (IPG) for generating the stimulating pulses under prescribed conditions and at least one lead bearing a stimulation electrode for delivering the stimulating pulses to the selected tissue. For example, cardiac pacemakers and ICDs have been developed for maintaining a desired heart rate during episodes of bradycardia or for applying cardioversion or defibrillation therapies to the heart upon detection of serious arrhythmias. Other nerve, brain, muscle and organ tissue stimulating medical devices are also known for treating a variety of conditions. The present invention will be described in relation to ICDs, but it is not intended that the invention be limited to that particular application when it can be advantageously implemented in other implantable medical devices.

In their simplest forms, cardiac pacemaker and ICD IPGs typically are formed having a metallic housing that is hermetically sealed and, therefore, is impervious to body fluids, and a header or connector assembly for making electrical and mechanical connection with one or more leads bearing pacing, sensing and cardioversion/defibrillation electrodes adapted to be located in or around selected chambers of the heart. Over the past 20 years, ICD IPGs have evolved, as described in some detail in commonly assigned U.S. Pat. No. 5,265,588, incorporated herein by reference in its entirety, from relatively bulky, crude, and short-lived IPGs simply providing high energy defibrillation shocks to complex, long-lived, and miniaturized IPGs providing a wide variety of pacing, cardioversion and defibrillation therapies. Numerous other programmable functions have been incorporated including enhanced capacity to detect and discriminate cardiac arrhythmias, data storage and uplink telemetry of data related to arrhythmia episodes and applied therapies, provision of staged therapies appropriate to the detected arrhythmia, for example. At the same time, numerous improvements have been made in cardioversion/defibrillation leads and electrodes that have enabled the cardioversion/defibrillation energy to be precisely delivered about selected upper and lower heart chambers and thereby dramatically reducing the delivered shock energy required to cardiovert or defibrillate the heart chamber. Moreover, the high voltage output circuitry has been improved in many respects to provide monophasic, biphasic, or multi-phase cardioversion/defibrillation shock or pulse waveforms that are efficacious, sometimes with particular combinations of cardioversion/defibrillation electrodes, in lowering the required shock energy to cardiovert or defibrillate the heart.

Throughout the course of development of these improvements, successive generations of such IPGs have always included common components located within the ICD IPG housing. These components include one or more battery, one or more high power cardioversion/defibrillation output capacitor, low voltage electronic circuitry powered by a battery for detecting and discriminating pathologic and/or nonpathologic arrhythmias from one another and providing other functions, and high voltage electronic charging circuitry for charging the output capacitor(s) from a battery voltage to a higher voltage and electronic switching circuitry for dumping the charge built up on the output capacitor(s) through the cardioversion/defibrillation electrodes. The charging circuitry typically comprises a DC-DC, "flyback" converter employing a bulky step-up transformer and switching circuitry of the type disclosed in the above-incorporated '588 patent that converts low battery voltage to a programmed high voltage that the output capacitor(s) are charged to.

It is widely understood that such ICD IPGs need to be small enough to be comfortably implanted subcutaneously without being unduly uncomfortable to the patient or cosmetically apparent. The first implanted automatic implantable defibrillator (AID) IPG housing disclosed in U.S. Pat. No. 4,254,775 was very large and had to be implanted in a patient's abdominal region. The two cylindrical output capacitors, the redundant, rectangular, high voltage batteries and the circuit boards bearing discrete components and integrated circuits (ICs) depicted in the '775 patent drawings are very bulky and assembled together by a framework that left a great deal of unused or unfilled space within the housing. These spaces exist because these components were only available in these shapes, whereas it is necessary to provide the IPG housing with rounded sides that provide more gradual transitions to prevent the housing edges from causing tissue erosion at the implant site.

Since that time, the ICs have been vastly reduced in size while their complexity has been vastly increased. Battery energy requirements for powering both the low voltage ICs and for providing the cardioversion/defibrillation shocks have been reduced while battery energy density has been increased and battery configuration made more conforming to the interior space of the IPG housing. Miniaturized, flat high voltage output capacitors that can be shaped to fit the allocated housing space and miniaturized high voltage switching components have been developed and employed. All of these improvements, together with the above-mentioned cardioversion/defibrillation improvements have contributed to a significant reduction in the volume of the IPG housing. Some of these improvements in capacitors and batteries are described in U.S. Pat. Nos. 5,370,663, 5,370, 669, 5,405,363, 5,527,346, 5,749,911, and 5,827,326, incorporated herein by reference. A space conserving, energy dissipation resistor is disclosed in U.S. Pat. No. 5,312,442, incorporated herein by reference in its entirety.

As these components are miniaturized to fit tightly within the confines of the ICD housing, the size and shape of the step-up transformer becomes a limiting factor on the thickness of the generally flat hermetically sealed ICD housing as shown in the above-incorporated '669 patent (transformer 76). Its bulk and shape can also lead to wasted space around it within the housing as shown in the above-incorporated '326 patent (FIG. 4).

It is a principal object of the present invention to provide further improvements in miniaturization of components employed within an IMD housing to fill one or more space within the housing interior that would otherwise not be occupied.

SUMMARY OF THE INVENTION

The present invention is directed to an IMD having a hermetically sealed chamber defined by a hermetically sealed housing, wherein the housing has an inner and an outer wall surface of a predetermined contour and enclosing a housing cavity. Contained within the housing cavity is a battery power source, a capacitor bank for storing a charge from the battery, and electronic circuitry coupled to the battery power supply and the capacitor bank for charging the capacitor bank through a step-up transformer and for discharging the capacitor bank into selected body tissue. A particular feature of the IMD of the present invention is that the step up transformer comprises a plurality of distributed core step-up transformer modules which are miniaturized sufficiently to fit within small spaces of the housing cavity. The plurality of distributed core, step-up transformer modules are amenable to being arranged to fit into spaces within the cavity of the IMD housing that are not otherwise occupied. The space otherwise occupied by the bulky, prior art step-up transformer can than be occupied by other components or can result in making the housing itself smaller and possibly thinner in profile than it would otherwise be.

In a preferred embodiment, the IMD is an ICD, the charging circuit and step-up transformer formed by the plurality of distributed core, and the step-up transformer modules constitute a DC-DC converter for converting low battery voltage to a cardioversion/defibrillation voltage stored in the capacitor bank. The discharging circuit is coupled with cardioversion/defibrillation electrodes located about or in the a patient's heart to discharge cardioversion/defibrillation shocks or pulses across the heart.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

The foregoing features, objects and advantages of the invention will become apparent to those skilled in the art from the following detailed description of a preferred embodiment, especially when considered in conjunction with the accompanying drawings in which:

FIG. 9 is a plan view of the location of components of the ICD IPG of FIGS. 1 and 2 showing the distributed core, step-up transformer modules of FIGS. 3 and 4 located therein.

DESCRIPTION OF THE PREFERRED EMBODIMENT OF THE INVENTION

The present invention can be implemented in any IMD requiring a transformer for providing a therapy and/or monitoring function. The present invention will be described in relation to an ICD IPG operating system design, but it is not intended that the invention be limited to that particular application when it can be advantageously implemented in other ICD IPG systems and in other IMDs.

Such ICD IPGs typically are formed having a housing that is hermetically sealed and, therefore, is impervious to body fluids, and a connector header for making electrical and mechanical connection with one or more leads bearing pacing, sensing and cardioversion/defibrillation electrodes adapted to be located in or around selected chambers of the heart. The housing is typically formed of a suitable, body-compatible material approved for medical use, such as titanium and is shaped physiologically so as to avoid sharp edges which might lead to tissue necrosis following implantation. Typically, the housing is formed having major opposed or parallel surfaces joined together by sides enclosing an interior housing chamber or cavity and having electrical feed-throughs extending therethrough and into the connector header. The housing cavity receives the battery(s) and the high voltage (HV) and low voltage (LV) electronic circuitry which can comprise ICs, hybrid circuits and discrete components, e.g., but not limited to, the step-up transformer and the high voltage output capacitor(s). Although, there is no particular preferred embodiment of such an ICD, FIGS. 1 and 2 depict one form of such an ICD in which the present invention can be advantageously implemented.

Figure 1:
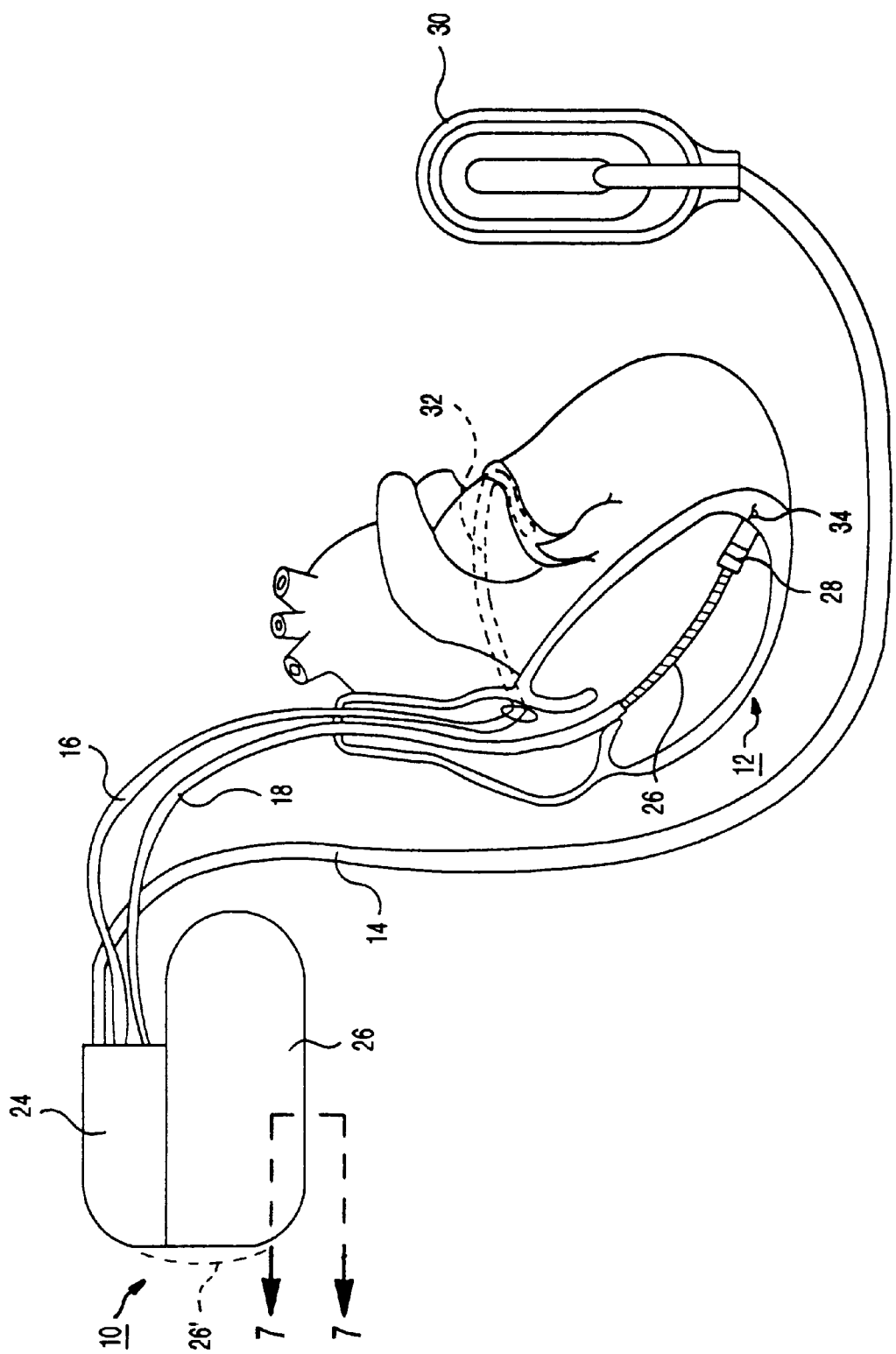
FIG. 1 illustrates the physical components of an ICD IPG and lead system extending to the heart of the type in which the present invention may be advantageously practiced.
Figure 2:
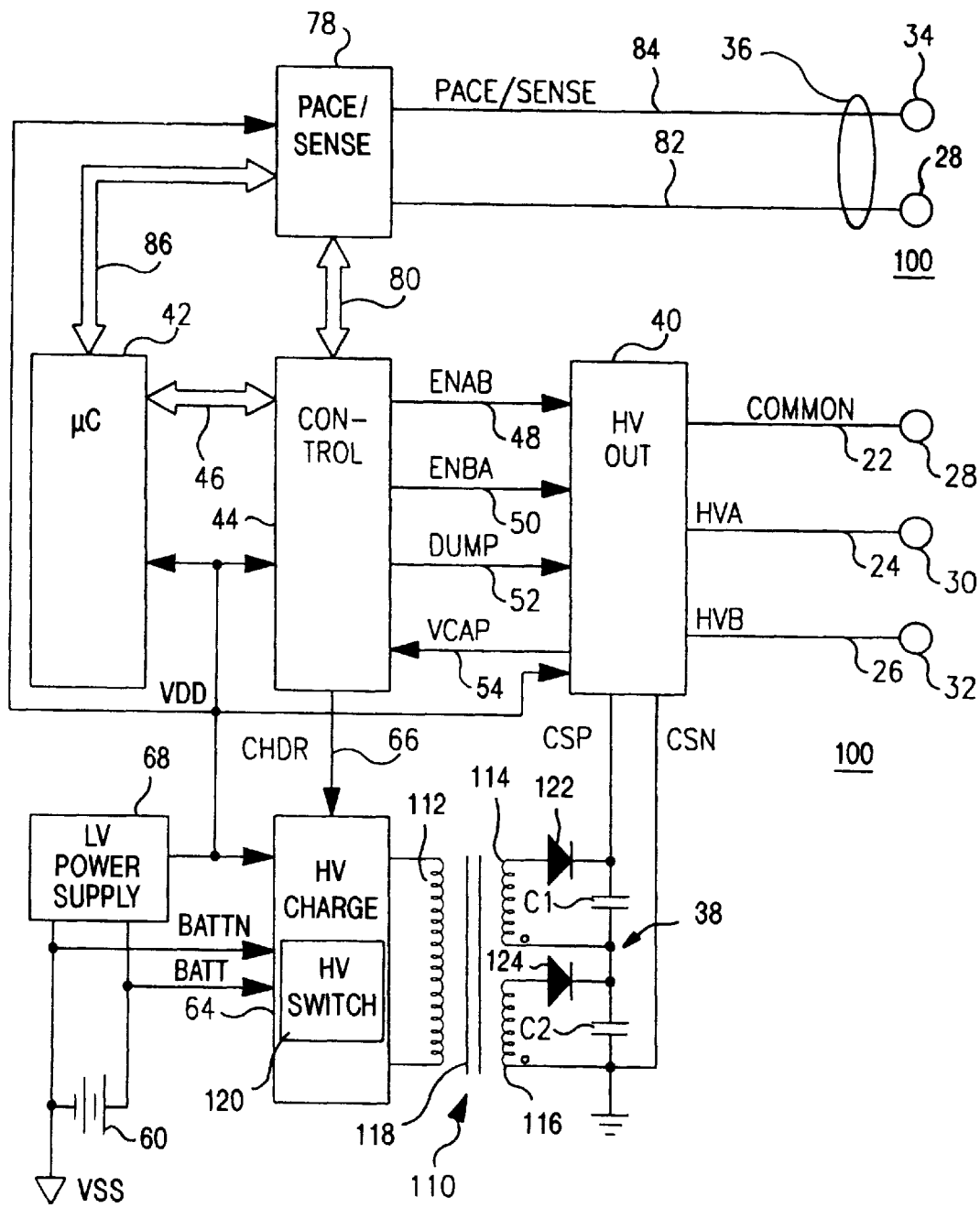
FIG. 2 is a functional block diagram illustrating a prior art ICD system having a conventional high voltage, single core, step-up transformer which can be advantageously modified to employ the distributed core, step-up transformer of the present invention occupying smaller spaces within the IPG housing cavity.

In FIG. 1, an ICD IPG 10 and associated 14, 16 and 18 are illustrated in relation to a patient's heart 12 as in FIG. 1 of the above-incorporated '588 patent. The IPG 10 comprises the hermetically sealed, metallic housing 36 and a multi-lumen connector header 24 which contains separate connector blocks and ports for receiving and electrically and mechanically attaching the proximal connector ends of the leads 14, 16 and 18. The feed-throughs (not shown) extend from the connector blocks (not shown) within the connector header 24 and the internal high voltage and low voltage circuitry within the housing 22 in a manner well known in the art.

The cardioversion/defibrillation leads 14, 16 and 18 bear relatively large surface area cardioversion/defibrillation electrodes 30, 32 and 26, respectively that are located in, on or about the heart 12. Cardioversion/defibrillation lead 14 extends subcutaneously and terminates distally in a subcutaneous electrode 30, which is intended to be mounted subcutaneously in the region of the left chest. Cardioversion/ defibrillation lead 16 extends transvenously and termninates distally in an elongated coil CS electrode 32 which is located in the coronary sinus and great vein region of the heart 12 and extends around the heart from a point within the opening of the coronary sinus to a point in the vicinity of the left atrial appendage. Ventricular cardioversion/defibrillation lead 18 extends transvenously and is provided with an elongated electrode coil 26 which is located in the right ventricular chamber of the heart 12. Cardioversion/defibrillation shocks can be applied between selected cardioversion/defibrillation electrodes.

The ICD IPG 10 preferably further incorporates atrial and/or ventricular EGM sensing capabilities for detecting atrial and/or ventricular arrhythmias and optionally providing for. Ventricular lead 18 also includes a ventricular pace/sense electrode 34 which takes the form of a helical coil which is screwed into the myocardial tissue of the right ventricle. Lead 18 may also include an additional pace/sense electrode 28 for near field ventricular EGM sensing or a surface electrode on the IPG 10 may be paired with the helical coil electrode 34 for far field ventricular EGM sensing. Additional near field and/or far field atrial EGM sensing and atrial pacing capabilities can be provided using atrial pace/sense electrode pairs on the atrial lead 16 and/or the IPG 10. A more detailed description of the leads illustrated can be found in commonly assigned U.S. Pat. No. 4,932,407, incorporated herein by reference in its entirety. The invention is also believed workable in the context of multiple lead and electrode systems appropriate for the treatment of the patient's arrhythmias.

In the system illustrated, ventricular cardiac pacing pulses are delivered between helical pace/sense electrode 34 and ring electrode 28. Pace/sense electrodes 28 and 34 are also employed to sense EGM signals characteristic of ventricular contractions. As illustrated, it is anticipated that the right ventricular cardioversion/defibrillation electrode 26 will serve as the common electrode during sequential and simultaneous pulse multiple electrode defibrillation regimens. For example, during a simultaneous pulse defibrillation regimen, shocks would simultaneously be delivered between cardioversion/defibrillation electrodes 26 and 30 and between cardioversion/defibrillation electrodes 26 and 32. During sequential pulse defibrillation, it is envisioned that shocks would be delivered sequentially between cardioversion/defibrillation electrodes 30 and 26 and between coronary sinus cardioversion/defibrillation electrode 32 and right ventricular cardioversion/defibrillation electrode 26. Single pulse, two electrode defibrillation pulse regimens may be also provided, typically between right ventricular cardioversion/defibrillation electrode 26 and coronary sinus cardioversion/defibrillation electrode 32. Alternatively, single pulses may be delivered between cardioversion/defibrillation electrodes 28 and 30. The particular interconnection of the cardioversion/defibrillation on electrodes to the ICD will depend somewhat on which specific cardioversion/defibrillation pulse regimen is employed.

FIG. 2 is a block diagram illustrating a prior art ICD system 100 having a conventional high voltage, single core, step-up transformer 110 which can be advantageously modified to employ the distributed transformer of the present invention as described further below. The ICD system 100 is merely exemplary of a variety of single chamber and dual chamber ICD systems having all or some of the capabilities described above in which the present invention can be implemented. The exemplary ICD system 100 includes a HV battery 60, a DC-DC converter comprising HV charging circuit 64, a HV single core transformer, a HV output capacitor bank 38, and a HV output or discharge circuit 40 for discharging the charge on the HV output capacitor bank 38. The charge on the HV output capacitor bank 38, comprising series connected capacitors C1 and C2 in this case, is selectively discharged through the cardioversion/defibrillation electrodes 26, 30 and 32 coupled via leads 22, 24 and 26 to the HV out circuitry 40. Similar ICD systems to that depicted in FIG. 2 in which the present invention can be implemented are shown, for example, in U.S. Pat. Nos. 4,830,006, 4,693,253, 4,971,058, 5,312,441, and 5,827,326, all incorporated herein by reference in their entireties, for example.

The exemplary prior art ICD system 100 of FIG. 2 is powered by the battery 60 coupled to the HV charging circuit 64 and to a power supply 68 which provides regulated power to the LV ICs, hybrid circuits, and discrete components of the system 100. Preferably, battery 60 is a lithium silver vanadium battery that can be employed to provide the HV capacitor charging current and that produces a voltage from about 3.2 volts when fresh to about 2.5 volts at specified end of service for a single chamber ICD and twice these values for a dual chamber ICD.

The LV ICs and hybrid circuits powered by supply voltage VDD (and other regulated voltages generated by LV power supply 68 in certain instances) comprise at least the illustrated microcomputer 42, the control and logic circuitry 44, and the pace/sense circuitry 78, and may include other circuits, e.g., a system clock, power-on-reset circuitry, telemetry circuitry, physiologic and activity sensing circuitry etc. The LV supply voltage VDD is also applied to the HV charging circuit 64 to power the DC-DC conversion switching circuits and to the HV output circuit 40 to power operation of certain circuitry therein.

As illustrated, the ICD system 100 is controlled by the operation of the microcomputer 42 and control circuitry 44 following an operating program stored in ROM and RAM which performs all necessary computational and control functions. Microcomputer 42 is linked to control circuitry 44 by means of a bi-directional data/control bus 46 and further interrupt and signal lines (not shown), and thereby controls operation of the HV output circuitry 40 and the HV charging circuitry 64. Pace/sense circuitry 78 awakens microcomputer 42 to perform any necessary mathematical calculations, to perform tachycardia and fibrillation detection procedures and to update the time intervals controlled by the timers in pace/sense circuitry 78 and control circuitry 44 upon receipt of a reprogramming command or on the occurrence of signals indicative of delivery of cardiac pacing pulses or the sensing of selected features of the EGM characteristic of cardiac contractions. The basic operation of such a system in the context of an implantable pacemaker/cardioverter/defibrillator may correspond to any of the systems known to the art, and in more particular may correspond generally to those illustrated in the above-incorporated '006, '253, and '441 patents for example.

Pace/sense circuitry 78 includes an R-wave sense amplifier according to the prior art as described in the above-incorporated '588 patent. Pace/sense circuitry 78 also includes a pulse generator for generating cardiac pacing pulses, which may also correspond to any known cardiac pacemaker output circuitry and includes timing circuitry for defining ventricular pacing intervals, refractory intervals and blanking intervals, under control of microcomputer 42 via control/data bus 86. Control signals triggering generation of cardiac pacing pulses by pace/sense circuitry 78 and signals indicative of the occurrence of R-waves from pace/sense circuitry 78 are communicated to control circuitry 44 by means of a bidirectional data bus 80. Pace/sense circuitry 78 is also coupled to ventricular pace/sense electrodes 28 and 34, illustrated in FIG. 1, by means of a conductors 82 and 84 in ventricular lead 36, allowing for bipolar sensing of R-waves and for delivery of bipolar pacing pulses to the ventricle of the heart 12. As noted above, dual chamber or single chamber atrial pacing and sensing functions can also or alternatively be provided employing suitable pace/sense circuitry 78 and suitable far field (unipolar) or near field (bipolar) atrial electrode pairs.

In this illustrated embodiment, the HV output circuitry 40 is coupled to the output capacitor bank 38, including capacitors C1 and C2, and is programmable for delivering biphasic cardioversion/defibrillation shocks to selected cardioversion/defibrillation electrodes. The output capacitors C1 and C2 are coupled to secondary windings 114 and 116 of step-up transformer 110 by means of the diodes 122 and 124. The primary winding 112 of step-up transformer 110 is coupled to the HV charging circuitry 64. The HV charging circuitry 64 is controlled by the CHDR signal on line 66 supplied by control circuitry 44 when a malignant arrhythmia subject to cardioversion/defibrillation therapy is detected. The output capacitors C1 and C2 are charged by oscillations of the high frequency, HV transformer 110 in the manner disclosed in detail in the above-incorporated '588 patent. The CSP and CSN voltage across the capacitor bank 38 is monitored and applied via the VCAP signal on line 54 to the control circuitry which detects the point when the VCAP signal level matches the programmed energy level of the cardioversion/defibrillation shock to be delivered. When that condition is satisfied, the control circuitry 44 terminates the CHDR signal and commences the operations to deliver the biphasic cardioversion/defibrillation shock to the selected cardioversion/defibrillation electrodes.

The control circuitry 44 provides three signals of primary importance to the HV output circuitry 40, namely the first control signal ENAB on line 48, the second control signal ENBA on line 50, and the DUMP signal on line 52 which initiates discharge of the charge stored across the output capacitors C1 and C2. The cardioversion/defibrillation electrodes 26, 30 and 32 illustrated in FIG. 1, above, are shown coupled to the output circuitry 40 by means of cardioversion/defibrillation leads 22, 24 and 26. For ease of understanding, these cardioversion/defibrillation leads are also labeled as "COMMON", "HVA" and "HVB". During a logic signal on ENAB, line 48, a cardioversion/defibrillation shock is delivered between electrode 30 and electrode 28. During a logic signal on ENBA, line 50, a cardioversion/defibrillation shock is delivered between cardioversion/defibrillation electrodes 32 and 26. However, other configurations are also possible. For example, subcutaneous cardioversion/defibrillation electrode 30 may be coupled to HVB conductor 26, to allow for a single pulse regimen to be delivered between electrodes 26 and 30. Moreover, the external surface of IPG housing 26 may be exposed and coupled as a remote subcutaneous cardioversion/defibrillation electrode replacing or augmenting the subcutaneous cardioversion/defibrillation electrode 30 and lead 24.

Figure 3:
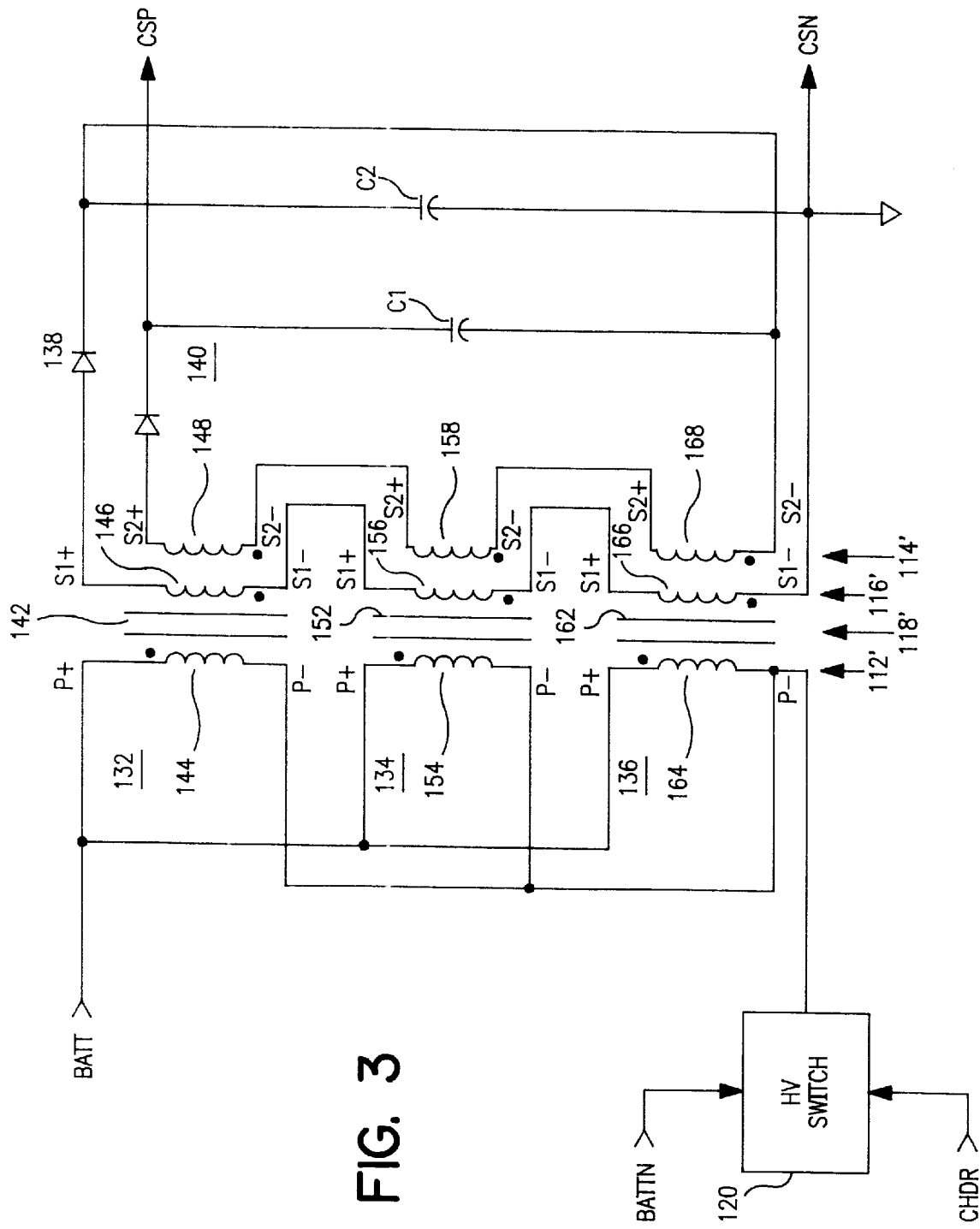
FIG. 3 is a schematic illustration of one embodiment of a distributed core step-up transformer comprising three distributed core, step-up transformer modules substituted for the single core, step-up transformer of FIG. 2.

The functions and detailed circuit schematics of the circuitry of FIG. 2 are set forth in the above-incorporated '588 patent. FIGS. 3 and 4a–4b of the '588 patent specifically illustrate the HV circuitry comprising the HV charging circuitry, 64, the HV output circuit 40 and the HV output transformer 110 and capacitor bank 38. With respect to the charging of the HV output capacitor bank 38, the primary winding 112 is coupled at one terminal to the power supply BATT input terminal through a fuse link and at its other terminal to the BATTN terminal through a duty cycle switching circuit block 120 described specifically in the above-incorporated '588 patent.

The switching circuit 120 includes a power FET transistor having its source and drain terminals coupled across a zener diode in such a fashion that when the power FET is rendered conductive by the CHGDR signal applied at its gate input terminal, it allows current to pass through the primary coil 112 of the HV step-up transformer 110. The power FET preferably has a very low drain-to-source impedance when conductive and a high gate impedance. A zener diode is coupled to the gate terminal of the power FET and has a reverse breakdown voltage of around 10 volts limits the CHGDR voltage. The switching of the power FET on and off effects the charging of the output capacitors C1, C2 in a well known "flyback" fashion. The manner of setting the frequency, duty cycle and amplitude of the CHGDR signal is immaterial to the present invention, and any such manner could be employed. The above-incorporated '588 patent sets forth a desirable way to do so.

To my knowledge, the prior art HV step-up transformer 110 employed in ICDs and other IMDs is formed with a single toroid or E—E shaped core 118 about which the primary winding 112 and secondary windings 114 and 116 are wound. In other ICD system configurations shown in the above-incorporated '006 patent, for example, additional windings about the common HV transformer core 118 have also been provided. As noted above, these prior art HV step-up transformers are relatively large in reference to the ICs and hybrid circuit substrates as well as the battery(s) and HV output patent (transformer 76).

FIG. 3 is a schematic illustration of the distributed core, HV step-up transformer 130 that can be substituted for the common core HV step-up transformer 110 of the ICD system 100 of FIG. 2 or similar IMD systems in accordance with the present invention. In accordance with the present invention, the bulky single HV transformer core 118 and the primary and secondary windings 112, 114 and 116 are replaced by a plurality of N distributed core step-up transformer modules comprising N distributed transformer core sets 118', N interconnected primary winding sets 112', N interconnected secondary winding sets 114' and N interconnected secondary winding sets 116'. In the illustrated embodiment, N=3, resulting in three distributed core, step-up transformer modules 132, 134 and 136, but it will be understood that N can be 2 or more. Each distributed core, step-up transformer module comprises a tubular or rod shaped magnetic core, a primary winding wound about the core and two secondary windings wound about the core. The distributed core, step-up transformer module 132 comprises a tubular or rod shaped magnetic core 142, a primary winding 144 wound about the core 142, and two secondary windings 146 and 148 wound about the core 142. The distributed core, step-up transformer module 134 comprises a tubular or rod shaped magnetic core 152, a primary winding 154 wound about the core 152, and two secondary windings 156 and 158 wound about the core 152. The distributed core, step-up transformer module 136 comprises a tubular or rod shaped magnetic core 162, a primary winding 164 wound about the core 162, and two secondary windings 166 and 168 wound about the core 162.

The primary winding set 112' is coupled with the HV switching circuit 120 and HV battery terminals BATT and BATTN, and the secondary winding sets are coupled to the series connected capacitors C1 and C2 through the diodes 140 and 138, respectively. The size, shape and material of each distributed magnetic core 142, 152, 162 and the primary and secondary winding wire diameter and turns about each core can be selected to provide the same functional current carrying and step-up ratio as the common core, HV step-up transformer 110.

However, each such distributed core, step-up transformer 132, 134, 136 can be fabricated in a reduced size and in a shape that allows it to be fitted into small spaces that other components may not be able to fit into. The distributed core, step-up transformer modules 132, 134, and 136 are amenable to being arranged to fit into spaces within the cavity of the ICD IPG housing 26 that are not otherwise occupied. The space otherwise occupied by the bulky, common core, HV step-up transformer 110 can than be used by other components or can result in making the housing itself smaller and possibly thinner in profile.

FIGS. 4 through 9 depict the best modes of practicing the present invention known to the inventor for fabricating the N reduced size, distributed core, step-up transformer modules and positioning them inside the housing cavity in relation to the other mechanical and electrical components of the exemplary ICD 10 and the major ICD system components depicted in FIGS. 1 and 2 and disclosed in the above-incorporated '588 patent.

Figure 4:
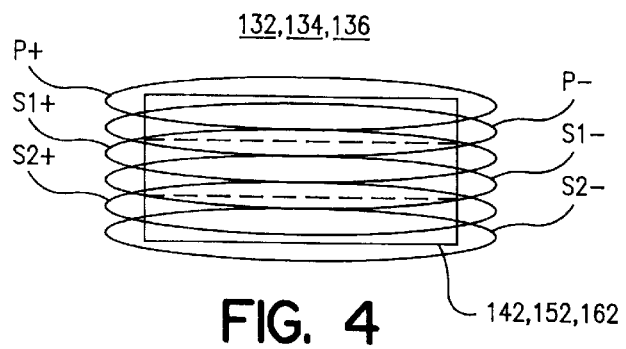
FIG. 4 is a schematic illustration of the distributed core, transformer modules of FIG. 3 of reduced size.
Figure 5:
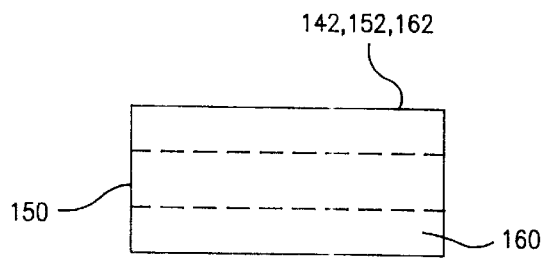
FIG. 5 is a side view of the magnetic rod core of the distributed core, transformer modules of FIG. 3.
Figure 6:
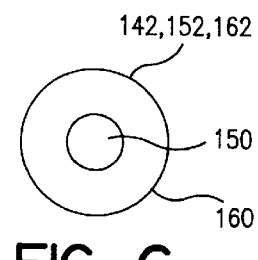
FIG. 6 is an end view of the magnetic rod core of FIG. 5.

FIG. 4 is a schematic illustration of the core and primary and secondary coil windings about the cores 142, 152, 162 of each of the distributed core, step-up transformer modules 132, 134, 136, respectively. FIGS. 5 and 6 depict exemplary magnetic rod cores 142, 152, 162 which are formed of molybdenum Permalloy or other soft magnetic powder, distributed gap, materials and can be obtained to some desired size and shape specification from Magnetics, Inc., Butler, Pa, or Arnold Engineering Co., Marengo, Ill. The elongated magnetic rod cores 142, 152, 162 can be formed with square, cylindrical and oval cross-section profiles as shown in FIGS. 5 and 6 and are formed with an axial bore 150 extending through their lengths. The length of the magnetic rod cores can be selected to fit the space available in the IMD housing and can vary from a very short length resulting in a toroidal shape to a longer length resulting in the depicted tubular shape. Preferably, the magnetic rod cores 142, 152, 162 are formed in the oval cross-section of FIG. 6 to have a major diameter and a minor diameter.

The primary and secondary coil windings, P+–P−, S1+–S1− and S+–S−, are wound through the axial bore 150 and around the exterior surface 160 in an overlying or interleaved winding pattern. The windings are distributed evenly around the circumference of the exterior surface 160 and extending through the axial bore 150. The primary coil windings P+–P− of each of the distributed core, step-up transformers are electrically connected in parallel as shown in FIG. 3. The secondary coil windings S1+–S1− and S+–S− of each of the distributed core, step-up transformers are electrically connected in series as shown in FIG. 3. The total primary inductance value $L_p$ of the parallel connected primary windings is related to the number of primary winding turns $N_p$ of each distributed core, step-up transformer module and the number of modules in accordance with the formula:

$$L_p \sim N_p^2 / \# modules$$

The total secondary inductance value $L_s$ of the each of the two series connected sets of the secondary coils is related to the number of secondary winding turns $N_s$ of each distributed core, step-up transformer module and the number of modules in accordance with the formula:

$$L_s \sim N_s^2 \times \# modules$$

Figure 7:
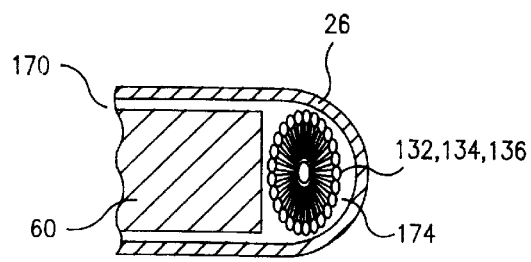
FIG. 7 is a cross-section view, taken along lines 7—7 of FIG. 1, illustrating the location of the distributed core, step-up transformer modules of FIGS. 3 and 4 in spaces around the side wall of the IMD housing that are typically unoccupied in the prior art.
Figure 8:
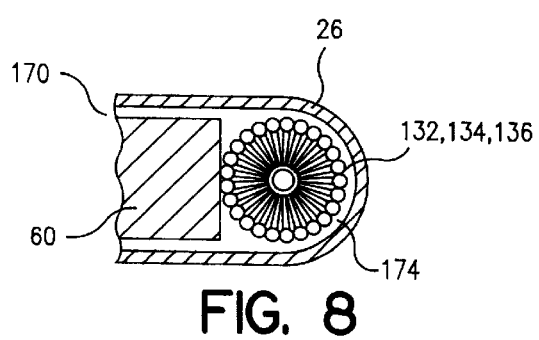
FIG. 8 is an alternative cross-section view, taken along lines 7—7 of FIG. 1, illustrating the location of the distributed core, step-up transformer modules of FIGS. 3 and 4 in spaces around the side wall of the IMD housing that are typically unoccupied in the prior art.

The cylindrical or the preferred oval shaped distributed core step-up transformer modules 132, 134, 136 can advantageously be arranged to lie within the housing cavity 170 along a relatively straight but convexly bowed outward side wall of the IPG housing 26. FIGS. 7 and 8 are cross-section views, taken along lines 7—7 of FIG. 1 illustrating the location of the distributed core, step-up transformer modules of FIGS. 3 and 4. in spaces around the side wall of the IMD housing that are typically unoccupied in the prior art. In FIG. 7, the oval major diameter is aligned in the width direction of the housing cavity 170 alongside and in a space not occupied by the battery or capacitor or circuitry, e.g., HV battery 60. This provides for minimal intrusion into the central part of the housing cavity 170. In FIG. 8, the oval minor diameter is aligned in the width direction of the housing cavity 170 alongside and in a space 174 not occupied by the battery or capacitor or circuitry, e.g., HV battery 60. This provides for minimal intrusion into the central part of the housing cavity 170 and for a thinner profile or width of the ICD housing 26.

FIG. 9 is a plan view of one embodiment of the location of components of the ICD IPG of FIGS. 1 and 2 showing the distributed core, step-up transformer modules 132, 134 and 136 of FIGS. 3 and 4 located within the previously unoccupied space 174 of the housing cavity 170 and in relation to the other major components. The other major components comprise the capacitors C1 and C2, the battery 60, the LV circuit board 184, the high voltage circuit board 186, (also possibly including spacers and retainers for holding these components in position) the feedthroughs 176, 178, 180 and 182 and electrical conductors connecting these components together (not shown). The three distributed core, step-up transformer modules 132, 134, and 136 are electrically connected to one another and to the HV circuit board 186 by a conductor assembly or cable 172 or the like. The cable 172 connects the primary and secondary windings of each such distributed core, step-up transformer module 132, 134, 136 together following the wiring diagram of FIG. 3.

Normally, the single core, step-up transformer 110 of FIG. 2 would be located on or adjacent to the HT circuit board in the space shown in the broken lines 110' in FIG. 9, as similarly depicted in FIG. 4 of the above-incorporated '363 patent, and would extend between the opposed major parallel surfaces of the housing 26. The size of the single core, step-up transformer 110 of FIG. 2 could dictate the thickness of the housing 26.

The substitution of the distributed core, step-up transformer modules 132, 134, and 136 in the space 174 may allow the housing 26 to be made smaller and thinner than the original housing 26' shown in broken lines in FIG. 9.

It will be understood that FIG. 9 merely depicts one example of how a plurality of the distributed core, step-up transformer modules could be incorporated into an IMD housing to use unoccupied space and/or make it smaller. The plurality of distributed core, step-up transformer modules could be located on the HV circuit board 186 of FIG. 9, for example.

Moreover, it will be understood that the plurality of distributed core, step-up transformer modules may constitute any number of 2 or more as required to meet performance specifications.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. An implantable medical device operable to perform a therapeutic and/or monitoring function comprising:

a housing having a housing side wall and inner and outer wall surfaces of a predetermined contour enclosing a hermetically sealed chamber; and electronic circuit means comprising a plurality of components sized to fit within said hermetically sealed chamber including a step-up transformer further comprising a plurality of distributed core, step-up transformer modules which are miniaturized sufficiently to fit within small spaces of the housing cavity and are electrically coupled together.

2. The implantable medical device as in claim 1, wherein the housing is formed with a curved side wall at least in part and the step-up transformer modules are amenable to being arranged to fit into spaces within the cavity of the housing adjacent curved side wall portions that are not otherwise occupied.

3. The implantable medical device as in claim 2, wherein the step-up transformer modules have a cross-section shaped to conform to the curvature of the curved side wall portions.

4. The implantable medical device as in claim 2, wherein the step-up transformer modules have an oval cross-section to conform to the curvature of the curved side wall portions.

5. The implantable medical device as in claim 1, wherein the step-up transformer modules are formed of magnetic rod cores with at least one primary winding and one secondary winding wound about each such magnetic rod core and further comprising circuit means for electrically connecting the primary windings of the step-up transformer modules together and for electrically connecting the secondary windings of the step-up transformer modules together.

6. The implantable medical device as in claim 5, wherein the step-up transformer modules are amenable to being arranged to fit into spaces within the cavity of the housing that are not otherwise occupied.

7. The implantable medical device as in claim 5, wherein the housing is formed with a curved side wall at least in part and the step-up transformer modules are amenable to being arranged to fit into spaces within the cavity of the housing adjacent curved side wall portions that are not otherwise occupied.

8. The implantable medical device as in claim 5, wherein the magnetic rod cores are formed of elongated tubular magnetic rods having a cross-section shaped to accommodate the at least one primary and secondary winding and to conform to the curvature of the curved side wall portions.

9. The implantable medical device as in claim 5, wherein the housing is formed with a curved side wall at least in part, the magnetic rod cores are formed of elongated tubular magnetic rods having a cross-section shaped to accommodate the at least one primary and secondary winding and to conform to the curvature of the curved side wall portions.

10. The implantable medical device as in claim 5, wherein the housing is formed with a curved side wall at least in part, the magnetic rod cores are formed of elongated tubular magnetic rods having an oval cross-section to accommodate the at least one primary and secondary winding and to conform to the curvature of the curved side wall portions.

11. An implantable tissue stimulating device comprising:

a housing having a housing side wall and inner and outer wall surfaces of a predetermined contour enclosing a hermetically sealed chamber;

a battery disposed within the sealed chamber;

capacitor means for storing a charge;

electronic circuit discharging means coupled with said capacitor means for discharging a voltage stored in said capacitor means into a tissue load; and electronic circuit charging means for charging said capacitor means to a voltage level prior to discharging the voltage stored in said capacitor means into a tissue load and further comprising a step-up transformer and switching circuit means coupled to said battery and said capacitor means, said step-up transformer further comprising a plurality of distributed core, step-up transformer modules which are miniaturized sufficiently to fit within small spaces of the housing cavity and are electrically coupled together.

12. The tissue stimulating device as in claim 11, wherein the housing is formed with a curved side wall at least in part and the step-up transformer modules are amenable to being arranged to fit into spaces within the cavity of the housing adjacent curved side wall portions that are not otherwise occupied.

13. The tissue stimulating device as in claim 12, wherein the step-up transformer modules have a cross-section shaped to conform to the curvature of the curved side wall portions.

14. The tissue stimulating device as in claim 12, wherein the step-up transformer modules have an oval cross-section to conform to the curvature of the curved side wall portions.

15. The tissue stimulating device as in claim 11, wherein the step-up transformer modules are formed of magnetic rod cores with at least one primary winding and one secondary winding wound about each such magnetic rod core and further comprising circuit means for electrically connecting the primary windings of the step-up transformer modules together and for electrically connecting the secondary windings of the step-up transformer modules together.

16. The tissue stimulating device as in claim 15, wherein the step-up transformer modules are amenable to being arranged to fit into spaces within the cavity of the housing that are not otherwise occupied.

17. The tissue stimulating device as in claim 15, wherein the housing is formed with a curved side wall at least in part and the step-up transformer modules are amenable to being arranged to fit into spaces within the cavity of the housing adjacent curved side wall portions that are not otherwise occupied.

18. The tissue stimulating device as in claim 15, wherein the magnetic rod cores are formed of elongated tubular magnetic rods having a cross-section shaped to accommodate the at least one primary and secondary winding and to conform to the curvature of the curved side wall portions.

19. The tissue stimulating device as in claim 15, wherein the housing is formed with a curved side wall at least in part, the magnetic rod cores are formed of elongated tubular magnetic rods having a cross-section shaped to accommodate the at least one primary and secondary winding and to conform to the curvature of the curved side wall portions.

20. The tissue stimulating device as in claim 15, wherein the housing is formed with a curved side wall at least in part, the magnetic rod cores are formed of elongated tubular magnetic rods having an oval cross-section to accommodate the at least one primary and secondary winding and to conform to the curvature of the curved side wall portions.

21. An implantable cardioverter/defibrillator for applying cardioversion/defibrillation shocks to a patient's heart comprising:

a hermetically sealed chamber defined by a housing having a housing side wall and inner and outer wall surfaces of a predetermined contour;

a battery disposed within the sealed chamber;

capacitor means for storing a cardioversion/defibrillation voltage;

means for charging said capacitor means to a cardioversion/defibrillation voltage level prior to discharging the voltage stored in said capacitor means into the heart as a cardioversion/defibrillation shock and further comprising a DC-DC converter for converting battery voltage to the cardioversion/defibrillation voltage through use of a step-up transformer and switching circuit means coupled to said battery and said capacitor means, said step-up transformer further comprising a plurality of distributed core, step-up transformer modules which are miniaturized sufficiently to fit within small spaces of the housing cavity and are electrically coupled together; and electronic circuit discharging means coupled with said capacitor means for discharging the cardioversion/defibrillation voltage stored in said capacitor means into the heart.

22. The cardioverter/defibrillator as in claim 21, wherein the housing is formed with a curved side wall at least in part and the step-up transformer modules are amenable to being arranged to fit into spaces within the cavity of the housing adjacent curved side wall portions that are not otherwise occupied.

23. The cardioverter/defibrillator as in claim 22, wherein the step-up transformer modules have a cross-section shaped to conform to the curvature of the curved side wall portions.

24. The cardioverter/defibrillator as in claim 22, wherein the step-up transformer modules have an oval cross-section to conform to the curvature of the curved side wall portions.

25. The cardioverter/defibrillator as in claim 21, wherein the step-up transformer modules are formed of magnetic rod cores with at least one primary winding and one secondary winding wound about each such magnetic rod core and further comprising circuit means for electrically connecting the primary windings of the step-up transformer modules together and for electrically connecting the secondary windings of the step-up transformer modules together.

26. The cardioverter/defibrillator as in claim 25, wherein the step-up transformer modules are amenable to being arranged to fit into spaces within the cavity of the housing that are not otherwise occupied.

27. The cardioverter/defibrillator as in claim 25, wherein the housing is formed with a curved side wall at least in part and the step-up transformer modules are amenable to being arranged to fit into spaces within the cavity of the housing adjacent curved side wall portions that are not otherwise occupied.

28. The cardioverter/defibrillator as in claim 25, wherein the magnetic rod cores are formed of elongated tubular magnetic rods having a cross-section shaped to accommodate the at least one primary and secondary winding and to conform to the curvature of the curved side wall portions.

29. The cardioverter/defibrillator as in claim 25, wherein the housing is formed with a curved side wall at least in part, the magnetic rod cores are formed of elongated tubular magnetic rods having a cross-section shaped to accommodate the at least one primary and secondary winding and to conform to the curvature of the curved side wall portions.

30. The cardioverter/defibrillator as in claim 25, wherein the housing is formed with a curved side wall at least in part, the magnetic rod cores are formed of elongated tubular magnetic rods having an oval cross-section to accommodate the at least one primary and secondary winding and to conform to the curvature of the curved side wall portions.

* * * * *